US009663756B1

(12) United States Patent
Lipkens et al.

(10) Patent No.: US 9,663,756 B1
(45) Date of Patent: May 30, 2017

(54) ACOUSTIC SEPARATION OF CELLULAR SUPPORTING MATERIALS FROM CULTURED CELLS

(71) Applicant: FloDesign Sonics, Inc., Wilbraham, MA (US)

(72) Inventors: Bart Lipkens, Hampden, MA (US); Rudolf Gilmanshin, Framingham, MA (US); Ben Ross-Johnsrud, Wilbraham, MA (US); Kedar Chitale, West Hartford, CT (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

(21) Appl. No.: 15/053,359

(22) Filed: Feb. 25, 2016

(51) Int. Cl.
*C12N 5/00* (2006.01)
*C12M 1/00* (2006.01)
(Continued)

(52) U.S. Cl.
CPC ............ *C12M 47/04* (2013.01); *C12M 33/00* (2013.01); *C12M 33/08* (2013.01); *C12M 47/02* (2013.01);
(Continued)

(58) Field of Classification Search
CPC ...... C12M 33/08; C12M 47/04; C12M 47/02; C12M 33/00; C12N 13/00; C12N 2527/00; C12N 5/0062
See application file for complete search history.

(56) References Cited

U.S. PATENT DOCUMENTS 2,473,971 A 6/1949 Ross
2,667,944 A 2/1954 Crites
(Continued)

OTHER PUBLICATIONS

Ding et al., Cell separation using tilted-angel standing surface acoustic waves. Proceedings of the National Academy of the Sciences, vol. 111, No. 36 (Sep. 9, 2014) pp. 12992-12997.*
(Continued)

*Primary Examiner* — Kara Johnson
(74) *Attorney, Agent, or Firm* — Fish & Richardson P.C.

(57) ABSTRACT

Methods, systems, and apparatus for acoustic separation of cellular supporting materials such as microcarriers or microbubbles from cell culture are provided. In one aspect, a method includes flowing a fluid containing the cellular supporting material and the cells through a flow chamber; driving at least one acoustic transducer to launch an acoustic wave from the acoustic transducer positioned on a first wall of the flow chamber to a reflector positioned on a second wall of the flow chamber to create, in the flow chamber, a multi-dimensional field that includes first spatial locales where acoustic pressure amplitude is elevated from a baseline level when the acoustic transducer is turned off, and second spatial locales where acoustic pressure amplitude is substantially identical to the baseline level when the acoustic transducer is turned off, wherein the first wall is opposite to the second wall; preferentially trapping, and gravity separating, the cellular supporting material or the cells at the first or second spatial locales inside the flow chamber; and collecting cells separated from the cellular supporting material using a first collection duct coupled to the flow chamber.

24 Claims, 9 Drawing Sheets

300
310
312
314
Flow Direction
321
320
302
308
304
Transducer
Reflector
306
323
308a
311
311

(51) Int. Cl.
*C12M 1/26* (2006.01)
*C12N 13/00* (2006.01)

(52) U.S. Cl.
CPC ............ *C12N 13/00* (2013.01); *C12N 5/0062* (2013.01); *C12N 2527/00* (2013.01)

(56) References Cited

U.S. PATENT DOCUMENTS 3,372,370 A 3/1968 Cyr
3,555,311 A 1/1971 Weber
4,055,491 A 10/1977 Porath/Furedi
4,065,875 A 1/1978 Srna
4,118,649 A 10/1978 Schwartzman et al.
4,158,629 A 6/1979 Sawyer
4,165,273 A 8/1979 Azarov et al.
4,173,725 A 11/1979 Asai et al.
4,204,096 A 5/1980 Barcus et al.
4,320,659 A 3/1982 Lynnworth et al.
4,344,448 A 8/1982 Potts
4,398,325 A 8/1983 Piaget et al.
4,666,595 A 5/1987 Graham
4,699,588 A 10/1987 Zinn et al.
4,743,361 A 5/1988 Schram
4,759,775 A 7/1988 Peterson et al.
4,800,316 A 1/1989 Wang
4,821,838 A 4/1989 Chen
4,836,684 A 6/1989 Javorik et al.
4,878,210 A 10/1989 Mitome
4,983,189 A 1/1991 Peterson et al.
5,164,094 A 11/1992 Stuckart
5,225,089 A 7/1993 Benes et al.
5,371,729 A 12/1994 Manna
5,395,592 A 3/1995 Bolleman et al.
5,431,817 A 7/1995 Braatz et al.
5,443,985 A 8/1995 Lu et al.
5,452,267 A 9/1995 Spevak
5,484,537 A 1/1996 Whitworth
5,527,460 A 6/1996 Trampler et al.
5,560,362 A 10/1996 Sliwa, Jr. et al.
5,594,165 A 1/1997 Madanshetty
5,604,301 A 2/1997 Mountford et al.
5,626,767 A 5/1997 Trampler et al.
5,688,405 A 11/1997 Dickinson et al.
5,711,888 A 1/1998 Trampler et al.
5,831,166 A 11/1998 Kozuka et al.
5,834,871 A 11/1998 Puskas
5,902,489 A 5/1999 Yasuda et al.
5,912,182 A 6/1999 Coakley et al.
5,951,456 A 9/1999 Scott
6,090,295 A 7/2000 Raghavarao et al.
6,166,231 A 12/2000 Hoeksema
6,205,848 B1 3/2001 Faber et al.
6,216,538 B1 4/2001 Yasuda et al.
6,273,262 B1 8/2001 Yasuda et al.
6,332,541 B1 12/2001 Coakley et al.
6,391,653 B1 5/2002 Letcher et al.
6,482,327 B1 11/2002 Mori et al.
6,487,095 B1 11/2002 Malik et al.
6,592,821 B1 7/2003 Wada et al.
6,649,069 B2 11/2003 DeAngelis
6,699,711 B1 3/2004 Hahn et al.
6,763,722 B2 7/2004 Fjield et al.
6,881,314 B1 4/2005 Wang et al.
6,929,750 B2 8/2005 Laurell et al.
6,936,151 B1 8/2005 Lock et al.
7,008,540 B1 3/2006 Weavers et al.
7,010,979 B2 3/2006 Scott
7,061,163 B2 6/2006 Nagahara et al.
7,081,192 B1 7/2006 Wang et al.
7,093,482 B2 8/2006 Berndt
7,108,137 B2 9/2006 Lal et al.
7,150,779 B2 12/2006 Meegan, Jr.
7,186,502 B2 3/2007 Vesey
7,191,787 B1 3/2007 Redeker et al.
7,322,431 B2 1/2008 Ratcliff
7,331,233 B2 2/2008 Scott
7,340,957 B2 3/2008 Kaduchak et al.
7,373,805 B2 5/2008 Hawkes et al.
7,541,166 B2 6/2009 Belgrader et al.
7,601,267 B2 10/2009 Haake et al.
7,673,516 B2 3/2010 Janssen et al.
7,837,040 B2 11/2010 Ward et al.
7,846,382 B2 12/2010 Strand et al.
7,968,049 B2 6/2011 Takahashi et al.
8,080,202 B2 12/2011 Takahashi et al.
8,134,705 B2 3/2012 Kaduchak et al.
8,256,076 B1 9/2012 Feller
8,266,950 B2 9/2012 Kaduchak et al.
8,273,302 B2 9/2012 Takahashi et al.
8,309,408 B2 11/2012 Ward et al.
8,319,398 B2 11/2012 Vivek et al.
8,334,133 B2 12/2012 Fedorov et al.
8,387,803 B2 3/2013 Thorslund et al.
8,592,204 B2 11/2013 Lipkens et al.
8,679,338 B2 3/2014 Rietman et al.
8,691,145 B2 4/2014 Dionne et al.
8,873,051 B2 10/2014 Kaduchak et al.
8,889,388 B2 11/2014 Wang et al.
8,956,538 B2 2/2015 Rietman et al.
9,011,699 B2 4/2015 Dionne et al.
9,228,183 B2 1/2016 Lipkens et al.
9,272,234 B2 3/2016 Lipkens et al.
9,340,435 B2 5/2016 Lipkens et al.
9,410,256 B2 8/2016 Dionne et al.
9,416,344 B2 8/2016 Lipkens et al.
9,422,328 B2 8/2016 Kennedy, III et al.
2002/0038662 A1 4/2002 Schuler et al.
2002/0134734 A1 9/2002 Campbell et al.
2003/0015035 A1 1/2003 Kaduchak et al.
2003/0028108 A1 2/2003 Miller et al.
2003/0195496 A1 10/2003 Maguire
2003/0209500 A1 11/2003 Kock et al.
2003/0230535 A1 12/2003 Affeld et al.
2004/0016699 A1 1/2004 Bayevsky
2004/0112841 A1 6/2004 Harold
2005/0031499 A1 2/2005 Meier
2005/0121269 A1 6/2005 Namduri
2005/0145567 A1 7/2005 Quintel et al.
2005/0196725 A1 9/2005 Fu
2006/0037915 A1 2/2006 Strand et al.
2006/0037916 A1 2/2006 Trampler
2007/0272618 A1 11/2007 Gou et al.
2007/0284299 A1 12/2007 Xu et al.
2008/0105625 A1 5/2008 Rosenberg et al.
2008/0217259 A1 9/2008 Siversson
2008/0245709 A1 10/2008 Kaduchak et al.
2008/0272034 A1 11/2008 Ferren et al.
2008/0272065 A1 11/2008 Johnson
2009/0029870 A1 1/2009 Ward et al.
2009/0045107 A1 2/2009 Ward et al.
2009/0053686 A1 2/2009 Ward et al.
2009/0087492 A1 4/2009 Johnson et al.
2009/0098027 A1 4/2009 Tabata et al.
2009/0104594 A1 4/2009 Webb
2009/0178716 A1 7/2009 Kaduchak et al.
2009/0194420 A1 8/2009 Mariella, Jr. et al.
2009/0295505 A1 12/2009 Mohammadi et al.
2010/0000945 A1 1/2010 Gavalas
2010/0078323 A1 4/2010 Takahashi et al.
2010/0078384 A1 4/2010 Yang
2010/0124142 A1 5/2010 Laugharn et al.
2010/0139377 A1 6/2010 Huang et al.
2010/0192693 A1 8/2010 Mudge et al.
2010/0193407 A1 8/2010 Steinberg et al.
2010/0206818 A1 8/2010 Leong et al.
2010/0255573 A1 10/2010 Bond et al.
2010/0261918 A1 10/2010 Chianelli et al.
2010/0317088 A1 12/2010 Radaelli et al.
2010/0323342 A1 12/2010 Gomez et al.
2010/0330633 A1 12/2010 Walther et al.
2011/0003350 A1 1/2011 Schafran et al.
2011/0024335 A1 2/2011 Ward et al.
2011/0092726 A1 4/2011 Clarke
2011/0095225 A1 4/2011 Eckelberry et al.

(56) References Cited

U.S. PATENT DOCUMENTS

| | | | |
|---|---|---|---|
| 2011/0123392 | A1 | 5/2011 | Dionne et al. |
| 2011/0125024 | A1 | 5/2011 | Mueller et al. |
| 2011/0146678 | A1 | 6/2011 | Ruecroft et al. |
| 2011/0154890 | A1 | 6/2011 | Holm et al. |
| 2011/0166551 | A1 | 7/2011 | Schafer |
| 2011/0189732 | A1 | 8/2011 | Wienand et al. |
| 2011/0262990 | A1 | 10/2011 | Wang et al. |
| 2011/0278218 | A1 | 11/2011 | Dionne et al. |
| 2011/0281319 | A1 | 11/2011 | Swayze et al. |
| 2011/0309020 | A1 | 12/2011 | Rietman et al. |
| 2012/0088295 | A1 | 4/2012 | Yasuda et al. |
| 2012/0163126 | A1 | 6/2012 | Campbell et al. |
| 2012/0175012 | A1 | 7/2012 | Goodwin et al. |
| 2012/0267288 | A1 | 10/2012 | Chen et al. |
| 2012/0325727 | A1 | 12/2012 | Dionne et al. |
| 2012/0325747 | A1 | 12/2012 | Reitman et al. |
| 2012/0328477 | A1 | 12/2012 | Dionne et al. |
| 2012/0329122 | A1 | 12/2012 | Lipkens et al. |
| 2013/0115664 | A1 | 5/2013 | Khanna et al. |
| 2013/0175226 | A1 | 7/2013 | Coussios et al. |
| 2013/0217113 | A1 | 8/2013 | Srinivasan et al. |
| 2013/0277316 | A1 | 10/2013 | Dutra et al. |
| 2013/0277317 | A1 | 10/2013 | LoRicco et al. |
| 2013/0284271 | A1 | 10/2013 | Lipkens et al. |
| 2014/0011240 | A1 | 1/2014 | Lipkens et al. |
| 2014/0017758 | A1 | 1/2014 | Kniep et al. |
| 2014/0080207 | A1 | 3/2014 | Lipkens et al. |
| 2014/0190889 | A1 | 7/2014 | Rietman et al. |
| 2014/0202876 | A1 | 7/2014 | Dionne et al. |
| 2014/0319077 | A1 | 10/2014 | Lipkens et al. |
| 2015/0158743 | A1 | 6/2015 | Rietman et al. |
| 2015/0176001 | A1 | 6/2015 | Lipkens et al. |
| 2016/0102284 | A1 | 4/2016 | Lipkens et al. |
| 2016/0129370 | A1 | 5/2016 | Lipkens et al. |
| 2016/0237394 | A1 | 8/2016 | Lipkens et al. |
| 2016/0237395 | A1 | 8/2016 | Lipkens et al. |

OTHER PUBLICATIONS

Junge et al., Cell detachment method using shock-wave-induced cavitation. Ultrasound in Medicine & Biology, vol. 29, No. 12 (Dec. 2003) pp. 1769-1776.*

Ohl et al., Detachment and sonoporation of adherent HeLa-cells by shock wave-induced cavitation. Biochimica et Biophysica Acta (BBA)-General Subjects, vol. 1624, No. 1-3 (Dec. 2003) pp. 131-138.*

* cited by examiner

ACOUSTIC SEPARATION OF CELLULAR SUPPORTING MATERIALS FROM CULTURED CELLS

CLAIM OF PRIORITY

This application claims priority under 35 USC §119(e) to U.S. Patent Application Serial No. 62/182,009, filed on Jun. 19, 2015, the entire contents of which are hereby incorporated by reference.

TECHNICAL FIELD

This disclosure relates to separation of cellular supporting materials such as microcarriers or microbubbles from cultured cells in bioreactors.

BACKGROUND

Cellular supporting materials such as microcarriers have been used for growing cultured cells in vitro. Cultured cells can be harvested from the cellular supporting materials, for example, by using proteolytic enzymes. Once the cells are separated from the cellular supporting materials, the issue remains to separate the cellular supporting materials from the now free-floating cells. It is therefore desirable to have a differential filtration process whereby the used cellular supporting materials may be separated from the cells that were formerly adhered to the surface of the cellular supporting materials.

SUMMARY

This disclosure describes technologies relating to methods, systems, and apparatus for acoustic separation of cellular supporting materials such as microcarriers or microbubbles from cultured cells in bioreactors, particularly using a multi-dimensional acoustic standing wave.

In general, one innovative aspect of the subject matter described in this specification can be embodied in a method of separating cellular supporting material from cells cultured on the cellular supporting material, the method including: flowing a fluid containing the cellular supporting material and the cells through a flow chamber; driving at least one acoustic transducer to launch an acoustic wave from the acoustic transducer positioned on a first wall of the flow chamber to a reflector positioned on a second wall of the flow chamber to create, in the flow chamber, a multi-dimensional field that includes first spatial locales where acoustic pressure amplitude is elevated compared to when the acoustic transducer is turned off, and second spatial locales where acoustic pressure amplitude is substantially identical to when the acoustic transducer is turned off, wherein the first wall is opposite to the second wall; preferentially trapping, the cellular supporting material or the cells at the first or second spatial locales inside the flow chamber; and collecting cells separated from the cellular supporting material using a first collection duct coupled to the flow chamber. Other implementations of this aspect include corresponding systems, apparatus, and computer programs, configured to perform the actions of the methods, encoded on computer storage devices.

These and other implementations can each optionally include one or more of the following features. For example, collecting cells may be performed without turning off the acoustic transducer. Preferentially trapping the cellular supporting material, the microcarriers, may include trapping in at least one of the first spatial locales or the second spatial locales to reduce a level of the cellular supporting material in the fluid.

The method may further include distinguishing between viable cells and non-viable cells based on at least one of compressibility, size, or density. The method may additionally include reducing an amount of the non-viable cells in fluid by preferentially trapping the non-viable cells. Preferentially trapping the non-viable cells may include preferentially trapping the non-viable cells at either the first spatial locales or the second spatial locales. The method may further include reducing an amount of the viable cells in the fluid by preferentially trapping the viable cells. The method may also include increasing a contrast factor between the viable and non-viable cells by changing acoustic properties of the either the viable or the non-viable cells. Changing the properties of either the viable or the non-viable cells may include changing cell volumes of viable cells by changing salt concentrations in the fluid.

The method may further include introducing an additive which enhances aggregation of the cellular supporting material into the flow chamber. The method may further include recirculating the cellular supporting material, such as microcarriers, to a culturing chamber coupled to the flow chamber. The method may also include: processing the collected cells for infusion into a subject patient. Subsequent to preferentially trapping, the method may include allowing the trapped cells or cell-supporting material to rise or settle out of the fluid due to a buoyance or gravity force and then exit the flow chamber.

The first and second spatial locales may be spaced along multiple trapping lines, each trapping line preferentially trapping the cellular supporting material or the cells in a direction at least partially perpendicular to a flow direction of the fluid flowing through the flow chamber. The cellular supporting material may include a particulate having a core that is more reflective than a shell of the particulate, and wherein preferentially trapping the cellular supporting material comprises preferentially trapping the particulate at one of the first spatial locales created inside the flow chamber. The cellular supporting material may include a particulate having a core that is less reflective than a shell of the particulate, and wherein the preferentially trapping the cellular supporting material comprises preferentially trapping the particulate at one of the second spatial locales created inside the flow chamber.

The method may further include flowing the fluid through the flow chamber vertically upwards, and collecting the cells via the first collection duct, wherein the cell-supporting material clump, cluster, or agglomerate such that the cell-supporting material sinks continuously or non-continuously down to a second collection duct coupled to the flow chamber, the second collection duct being different from the first collection duct.

The method may also include flowing the fluid through the flow chamber vertically downwards, and collecting the cells via the first collection duct and the cell-supporting material settle to a second collection duct coupled to the flow chamber, the second collection duct being different from the first collection duct.

The particulates may include microcarriers, and wherein at least one of the microcarriers comprises a sphere with a diameter of about 20 to 300 μm and comprises at least one of DEAE (N, N-diethylaminoethyl)-dextran, glass, polystyrene plastic, acrylamide, collagen, or alginate. The cell-supporting material may include microbubbles that have a surface coating for growth of the cells. The cells may include T-cells, MRC-5 cells or stem cells.

In another aspect, some implementations provide a system for separating cellular supporting material from cells cultured on the cellular material, the system including a flow chamber configured to accept a fluid containing the cellular supporting material and the cells; at least one acoustic transducer positioned on a first wall of the flow chamber and configured to launch an acoustic wave when driven by a power signal; at least one reflector positioned on a second wall of the flow chamber, the second wall opposite to the first wall, the reflector configured to reflect the acoustic wave such that a multi-dimensional acoustic field that includes first spatial locales where acoustic pressure amplitude is elevated from a baseline level when the acoustic transducer is turned off, and second spatial locales where acoustic pressure amplitude is substantially identical to the baseline level when the acoustic transducer is turned off; a first collection duct coupled to the flow chamber and configured to collect cells separated from the cellular supporting material after at least a portion of either the cellular supporting material or the cells have been trapped at the first or second spatial locales, both spatial locales having been created inside the flow chamber.

These and other implementations can each optionally include one or more of the following features. For example, the system may further include: multiple trapping lines from the multi-dimensional acoustic standing wave inside the flow chamber, each trapping line preferentially trapping the cellular supporting material or the cells in a direction at least partially perpendicular to a flow direction of the fluid flowing through the flow chamber.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure describes methods, systems and apparatus for using a multi-dimensional acoustic standing wave with nodes and antinodes for separation of cellular supporting materials such as microcarriers or coated microbubbles from cells in a bioreactor or other process, where the cells have been adherent to, cultured on, and cleaved from the cellular supporting materials prior to the separation.

The multi-dimensional acoustic standing wave can give rise to a spatial pattern of acoustic radiation force. The multidimensional acoustic standing wave may be generated from one transducer and reflector pair due to the multimode perturbations of the piezoelectric material in the transducer. The acoustic radiation force can have an axial force component and a lateral force component that are of the same order of magnitude. The spatial pattern may manifest as periodic variations of radiation force. More specifically, pressure node planes and pressure anti-node planes can be created in a fluid medium that respectively correspond to floor acoustic radiation force planes with maximum and minimum acoustic radiation force planes in between pressure nodal and anti-nodal planes. Pressure nodal planes are also acoustic displacement anti-nodal planes, and vice versa. The spatial pattern may function much like a comb filter in the fluid medium to trap particles of a particular size or size range, while particles of a different size or size range may not be trapped. Moreover, in a multidimensional acoustic standing wave the acoustic radiation forces within a particular pressure nodal plane are such that particles are trapped at several distinct points within these planes. The trapping of particles leads to the formation of cluster of particles, which continuously grow in size, and, upon reaching a critical size, settle out or rise out of the primary fluid continuously because of enhanced gravitation or buoyancy settling. For example, the spatial pattern can be configured, for example, by adjusting the insonification frequency, power of the transducer, or fluid velocity, to allow the cultured cells to freely flow through while trapping the cellular supporting materials, such as microcarriers or microbubbles, thereby separating at least the trapped cellular supporting material from the cells.

The separation may be leveraged to harvest cultured cells after the cells have been cleaved from cellular supporting materials, such that the extracted cells may be infused into a patient. Using the multi-dimensional acoustic standing wave to separate the cellular supporting materials from the cultured cells can be applicable to a variety of cell therapy applications, e.g., vaccine therapies, stem cell therapies, particularly allogenic and autologous therapies, or regenerative therapies.

Figure 1:
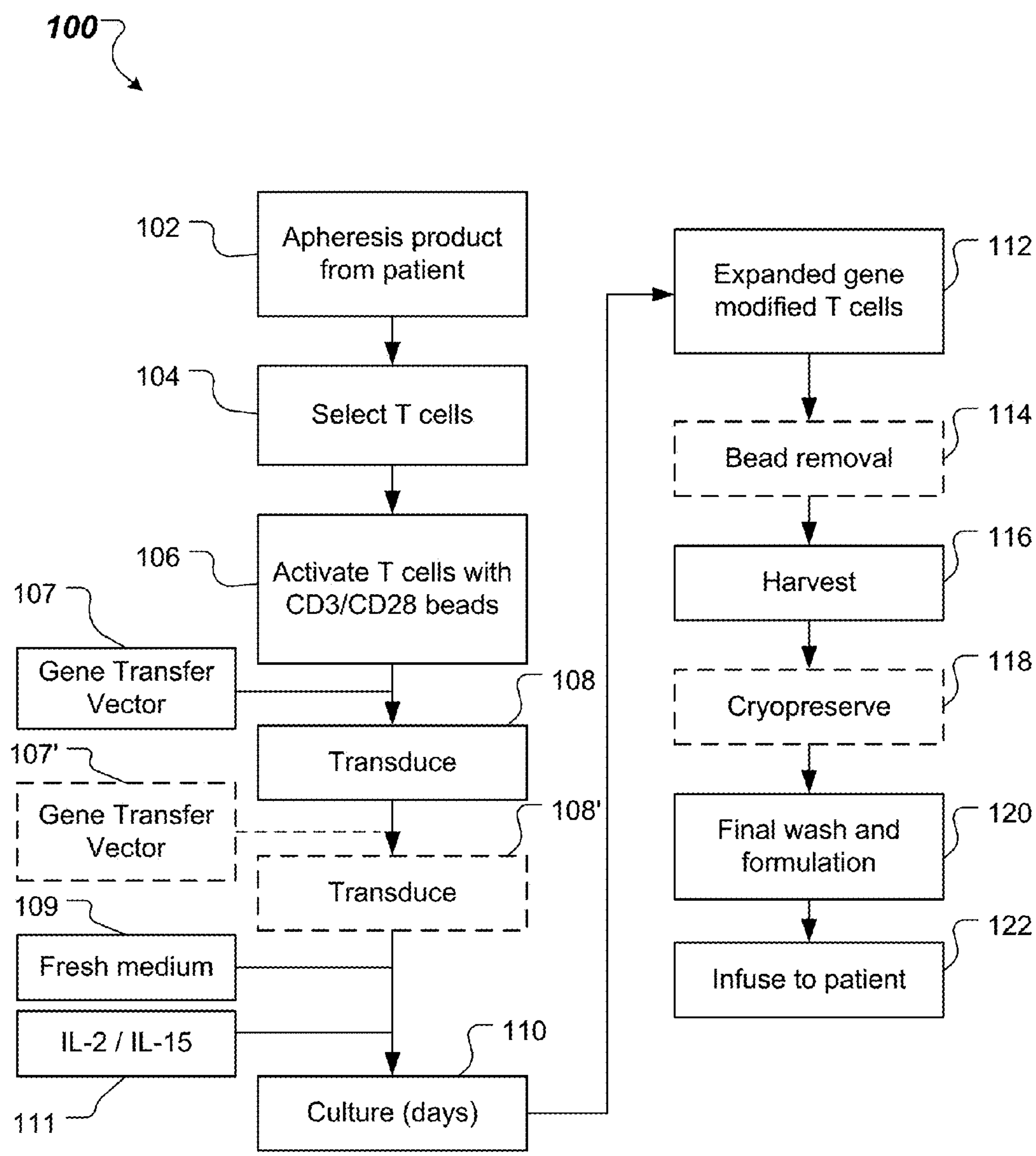
FIG. 1 is a schematic diagram showing an example of product manufacturing and testing process using microcarriers for cell therapy.

FIG. 1 is a schematic diagram showing an example product manufacturing and testing process 100 for cell therapy, e.g., production of modified adherent cells using microcarriers and separation of the microcarriers from cells using acoustophoresis. As an example, microcarriers such as beads have been used here as cellular supporting materials. Other cellular supporting materials such as coated bubbles or microbubbles can be also used for cell therapy.

Apheresis product is obtained from a patient (102). For example, a whole blood sample of the patient can be passed through an apparatus, e.g., a centrifuge that spins out components, e.g., plasma, leukocytes, and erythrocytes, and returns leukocytes as well as the remainder fraction of erythrocytes and plasma to the circulation. Adherent cells (for example, T lymphocytes or mammalian cells) may be a type of lymphocyte (in turn, a type of white blood cell) or mammalian cell that plays a central role in cell-mediated immunity. The adherent cells can be selected (104) from the separated components, that is, the apheresis product. In this disclosure, adherent cells are used as an illustrative example. The principle equally applies to other cells for therapy.

Next, the adherent cells are bound to (106) microcarriers, e.g., CD3/CD28 activated beads. As discussed in further details below, e.g., in FIGS. 2A and 2B, the microcarriers can be functionalized with surface chemistry such that the adherent cells can be attached or adherent to the surface of the microcarriers. The microcarriers can include support matrices allowing for the growth of adherent cells in bioreactors. In some cases, adherent cells will bind to the microcarriers without the antigens on the surface and the microcarriers can be functionalized or non-functionalized.

In a transduction process (108), genetic material, e.g., DNA or siRNA, is inserted into the adherent cells, e.g., by the use of gene transfer vector 107 such a, electroporation, or chemical reagents that increase cell permeability. In some implementations, to insert an additional genetic material into the adherent cells, an additional transduction process 108' can be executed with the use of an additional gene transfer vector 107'.

After transduction, fresh fluid medium 109 such as bioreactors can be added to the gene-modified adherent cells for cell culture. Interleukin 2 (IL-2)/Interleukin 15 (IL-15) 111 can be also added into the fresh fluid medium 109 for the gene-modified adherent cells, which can prevent autoimmune diseases by promoting the differentiation of certain immature adherent cells into regulatory adherent cells when the adherent cells mature.

The gene-modified adherent cells are cultured (110) in vitro on the surface of microcarriers that function as a vehicle for carrying the adherent cells in the fluid medium with IL-2/IL-15. The cell culture can last for several days. During this period, the adherent cells can be grown under controlled conditions, to eventually obtain expanded gene-modified adherent cells (112).

To separate cultured adherent cells from the microcarriers where the adherent cells are adhered to the microcarriers, the cultured adherent cells can be first cleaved from the microcarriers, e.g., by the use of proteolytic enzymes such as trypsin or collagenase. In one example, once the adherent cells have been cleaved from the microcarriers, the fluid medium becomes a mixture of suspended microcarriers and free-floating adherent cells in the fluid solution.

The microcarriers may then be removed from the fluid medium (114) thus separated from the cultured adherent cells. The separation of the microcarriers from the cultured adherent cells is an interesting feature of the production cycle. As discussed in further details below, e.g., in FIGS. 3A-3D, acoustophoresis can be utilized for the microcarrier removal by tuning a multi-dimensional acoustic standing wave that includes nodal regions and anti-nodal regions to trap the microcarriers and allow the adherent cells that have been separated from the microcarriers to flow through the fluid stream. This process can be advantageous for separating the microcarrier substrate from the target cells compared to other physical filtration methods.

Thereafter, the T-cells are harvested (116), e.g., by separating the cultured T-cells from the growing fluid medium. Several techniques can be used to perform the operation: centrifugation, microfiltration, depth filtration, and filtration through absolute pore size membranes. In a particular example, centrifugation is used for the harvesting process. One or more product release tests can be also performed, including flow cytometry (phenotype/ScFv), residual bead count, potency for cytokine production, vector copy number (PCR), mycoplasma control, and/or replication-competent vector (PCR+culture).

Subsequently, the T-cells are cryopreserved (118), e.g., by cooling to sub-zero (Celsius) temperatures to preserve the T-cells that may be susceptible to damage caused by chemical reactivity or time. Viability/cell count tests may be carried out for the T-cells. Final wash and formulation of the T-cells are performed (120). After that, sterility (bacterial and fungal mycoplasma) and/or endotoxin tests are performed before eventually the harvested cells are infused to the patient (122).

Figure 2A:
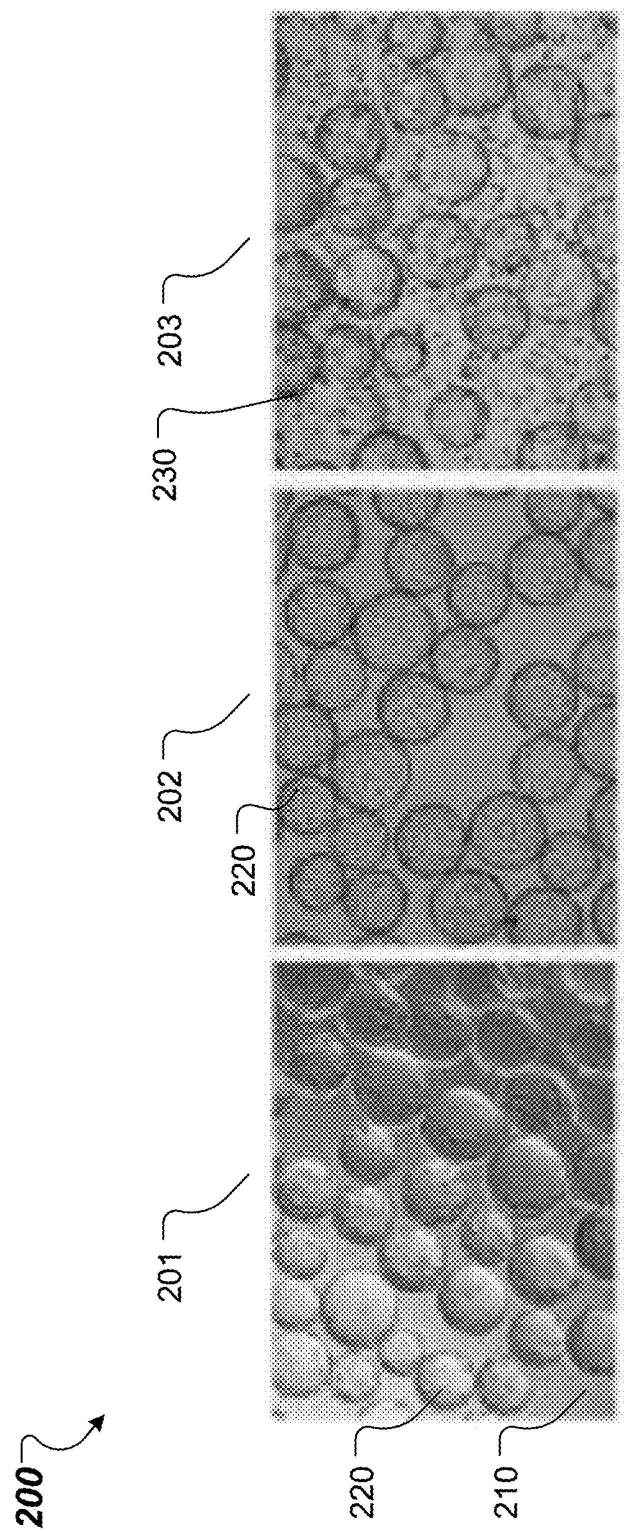
FIG. 2A shows an example of a process of adherent cells binding to microcarriers.
Figure 2B:
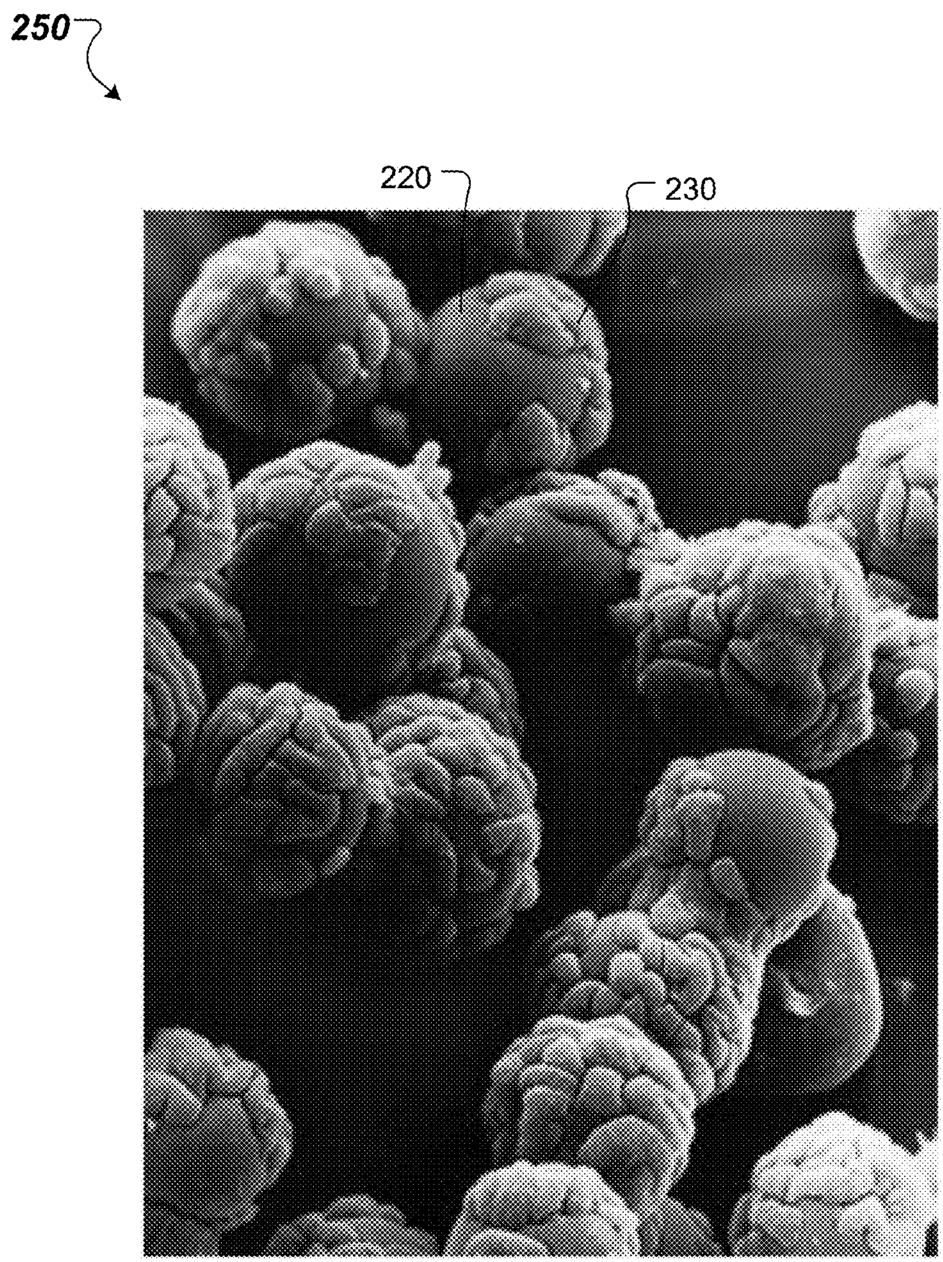
FIG. 2B shows an example of adherent cells attached to microcarriers.

FIG. 2A shows an example process 200 of adherent cells 230 binding to microcarriers 220 in a bioreactor 210, which can be used in the activation step 106 of the process 100 of FIG. 1. FIG. 2A shows the microcarriers 220 in a translucent light before (201), during (202), and after (203) the attachment of the adherent cells 230. FIG. 2B shows an example 250 of adherent cells 230 attached to microcarriers 220 after the binding. As noted above and below, the microcarriers 220 can include support matrices allowing for the growth of adherent cells 230 in the bioreactor 210.

Structurally, the microcarriers include spheres with a diameter in a range of 90 to 300 μm, e.g., in the range of 125 to 250 μm. The spheres can have densities in a range of 1.02-1.10 g/cm$^3$, such that the spheres may be maintained in suspension with gentle stirring. In some instances, the microcarriers can also include rod-like structures. The microcarriers generally are smooth or macroporous.

The core of the microcarriers can be made from different materials, such as glass, polystyrene plastic, acrylamide, collagen, and alginate. The microcarrier materials, along with different surface chemistries, can influence cellular behavior, including morphology and proliferation.

The microcarriers can be designed with a surface chemistry which allows for attachment and growth of anchorage dependent cell lines. The microcarriers can have smooth and nonporous surfaces, such that the cell filipodia dissolve quickly when cleaved from the microcarriers. Cells harvested from smooth microcarriers can be more robust and viable for a next stage of a production process by virtue of the non-invasive and non-contact filter operation characteristics. Also, the microcarriers can have a large ratio of surface area to volume for cell culture. The microcarriers can be coated with a variety of coatings such as glass, collagen (e.g., neutral or charged gelatin), recombinant proteins or chemical treatments to enhance cell attachment, which may lead to more desirable cell yields for a number of different cell lines.

Surface chemistries for the microcarriers can include extracellular matrix proteins, recombinant proteins, peptides, and positively or negatively charged molecules. The surface charges of the micro carriers may be introduced from a number of different groups, including DEAE (N, N-diethylaminoethyl)-dextran, laminin or vitronectin coating (extra cellular matrix proteins). In the DEAE-dextran example, a mild positive charge can be added to the surface.

In some implementations, the microcarriers are formed by substituting a cross-linked dextran matrix with positively charged DEAE groups distributed throughout the matrix. This type of microcarrier can be used for established cell lines and for production of viruses or cell products from cultures of primary cells and normal diploid cell strains.

In some implementations, the microcarriers are formed by chemically coupling a thin layer of denatured collagen to the cross-linked dextran matrix. Since the collagen surface layer can be digested by a variety of proteolytic enzymes, it provides opportunities for harvesting cells from the microcarriers while maintaining maximum cell viability and membrane integrity.

The microcarrier technology described here can be used in high density cell culture, new research applications, large production culture volumes, e.g., more than 1,000 liters, efficient monitoring and culture control, reduction of costs and contamination in cell culture applications.

Figure 3A:
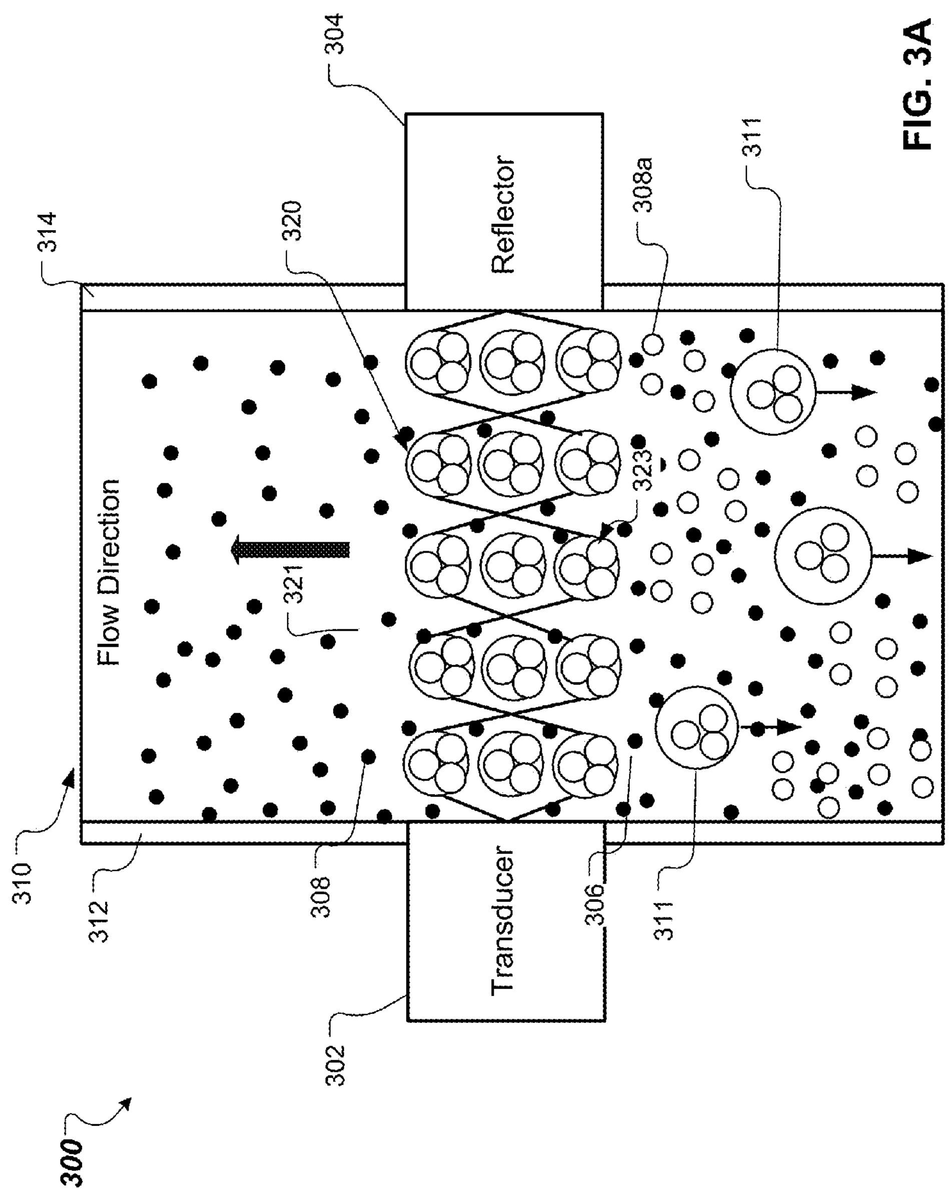
FIG. 3A shows a schematic diagram of an apparatus in which multi-dimensional field distribution is created in a flow chamber to effectuate separation of cells from cellular supporting material in a fluid.

FIG. 3A shows a schematic diagram of an apparatus 300 in which a multi-dimensional acoustic standing wave is created in a flow chamber to effectuate separation of microcarriers from adherent cells in a fluid. Example adherent cells may include human multipotent stem cells (hMSC), human mesenchymal stem cells (also hMSC), human pluripotent stem cells (hPSC), human dermal fibroblasts (hDF), human chondrocytes, and some T lymphocytes. Adherent cells may differ in their antigen specificity (e.g. CD8 adherent cell). The lines used in cell therapy may be mono- or polyclonal (e.g. polyclonal CD8 adherent cell line), and CAR adherent cells (a.k.a. artificial adherent cell receptors, or chimeric adherent cell receptors, or chimeric immunoreceptors. These are T-cells modified to recognize a specific protein. CAR=chimeric antigen receptor). The adherent cells have been previously adhered to and cultured on the microcarriers but cleaved therefrom prior to entry into the flow chamber. The apparatus 300 can be used for the microcarrier removal step 114 of the cell therapy process 100 of FIG. 1. The apparatus 300 can be an acoustophoretic separator as described in U.S. application Ser. No. 14/026,413 entitled "ACOUSTOPHORETIC SEPARATION TECHNOLOGY USING MULTI-DIMENSIONAL STANDING WAVES," and/or U.S. application Ser. No. 14/313,813 entitled "FLUID DYNAMIC SONIC SEPARATOR," whose contents are hereby incorporated by reference in their entirety.

The apparatus 300 includes a flow chamber 310 that has at least one inlet for receiving the mixture of suspended microcarriers 308 and free-floating cells 308*a* in the fluid 306. An acoustic transducer 302 is positioned on a wall 312 of the flow chamber 310 and configured to generate an acoustic wave when driven by a power signal. A suspended microcarrier 308 can be an agglomerate 311 that includes more than one microcarrier. A reflector 304 positioned on a wall 314 opposite to the wall 312 of the flow chamber and configured to reflect the acoustic wave such that a multi-dimensional acoustic standing wave 320 is created within the flow chamber 310 and between the acoustic transducer 302 and the reflector 304. The multi-dimensional acoustic standing wave 320 may represent a multi-dimensional acoustic standing wave that is without a travelling component (or with a minimal traveling wave component). Such a field distribution includes first spatial locales inside the flow chamber where acoustic pressure amplitude increases compared to when the acoustic transducer 302 is turned off, as well as second spatial locales inside the flow chamber where acoustic pressure amplitude is substantially identical to when the acoustic transducer 302 is turned off. In this context, the pressure/intensity changes may not be ephemeral. Rather, such changes may be stable and represent stabilized outcome of pressure/intensity. In one illustration, the increase may represent a stable densification of medium density while a decrease may represent a stable rarefaction of medium density. In another illustration, the first spatial locales correspond to nodal regions while the second spatial locales correspond to anti-nodal regions. Further, multi-dimensional refers to more than one dimension.

The acoustic transducer 302 and the reflector 304 can be positioned such that the axial direction of the multi-dimensional acoustic standing wave is at least partially perpendicular to a flow direction of the mixture flowing through the flow chamber 310. In one instance, the axial direction of the multi-dimensional acoustic standing wave is substantially perpendicular to a flow direction of the mixture flowing through the flow chamber 310. Here, the axial direction refers to the direction of a travelling wave that gives rise to the standing wave. In the context of longitudinal waves such as acoustic waves, the axial direction may be orthogonal to a transverse direction.

As discussed in further details below, the multidimensional acoustic standing wave allows for trapping of microcarriers that then agglomerate and clump at hot spots and continuously separate due to gravity or buoyance forces, while the adherent cells are allowed to freely flowing through the flow chamber 310 into a subsequent chamber or container for collection. In some example, microcarriers with a reflective core that bounces incident acoustic standing waves have a positive contrast factor. Such microcarriers may be driven by the acoustic radiation force to the pressure nodal hot spots within the pressure planes. Microcarriers with an absorbent core may accept incident acoustic standing waves more than bouncing these waves. Such microcarriers may have a negative contrast factor, and may be driven by the acoustic radiation force to the pressure anti-nodal planes. The cells, on the other hand, are not trapped by the insonification process and can flow with the fluid medium.

The acoustic transducer 302 includes a vibrating material such as a piezoelectric material, e.g., PZT-8. The acoustic transducer 302 can be configured such that, when driven by a voltage signal, e.g., sinusoidal, pulsed, square, with a frequency of 100 kHz to 10 MHz, the vibrating material is vibrated at a higher order vibration mode to generate an acoustic wave that is reflected by the reflector 304 to create a multi-dimensional acoustic standing wave. That is, the acoustic wave is generated by a higher order mode perturbation of the vibrating material. In some cases, the acoustic wave is a multiple component wave generated by the higher order mode perturbation of the vibration material. In some cases, the acoustic wave is a combination of a multiple component wave generated by the higher order mode perturbation of the vibration material and a planar wave generated by a piston motion of the vibration material. The higher order vibration mode can be in a general formula (m, n), where m and n are an integer and at least one of m or n is greater than 1. In a particular example, the acoustic transducer 302 vibrates in higher order vibration modes than (2, 2), which produce more nodes and antinodes, resulting in three-dimensional standing waves in the flow chamber 310. In another example, acoustic transducer 302 may also experience higher order vibration mode when 4 modes are distributed in a circular pattern on the surface of the acoustic transducer 302 with an additional mode in the middle.

The acoustic transducer 302 can be variably configured to generate higher order vibration modes. In some implementations, the vibrating material is configured to have an outer surface directly exposed to a fluid layer, e.g., the mixture of microcarriers and cultured cells in a fluid flowing through the flow chamber. In some implementations, the acoustic transducer includes a wear surface material covering an outer surface of the vibrating material, the wear surface material having a thickness of a half wavelength or less and/or being a urethane, epoxy, or silicone coating, polymer, or similar thin coating. In some implementations, the acoustic transducer includes a housing having a top end, a bottom end, and an interior volume. The vibrating material can be positioned at the bottom end of the housing and within the interior volume and has an interior surface facing to the top end of the housing. In some examples, the interior surface of the acoustic material is directly exposed to the top end housing. In some examples, the acoustic transducer includes a backing layer contacting the interior surface of the acoustic material, the backing layer being made of a substantially acoustically transparent material. One or more of the configurations can be also combined in the acoustic transducer 302 to be used for generation of a multi-dimensional acoustic standing wave.

The generated multi-dimensional acoustic standing wave can be characterized by strong gradients in the acoustic field in all directions, not only in the axial direction of the standing waves but also in the lateral directions. In some instances, the strengths of such gradients are such that the acoustic radiation force is sufficient to overcome drag forces at linear velocities on the order of mm/s. Particularly, an acoustic radiation force can have an axial force component and a lateral force component that are of the same order of magnitude. As a consequence, the acoustic gradients result in strong trapping forces in the lateral direction. The multi-dimensional acoustic standing wave 320 can result in a pressure field with hot spots at multiple maxima 321 and minima 323 of acoustic displacement, and the pressure field has pressure nodal planes including the hot spots at the minima of the acoustic radiation potential and pressure anti-nodal planes including the hot spots at the maxima of the acoustic radiation potential for particles with positive contrast factor. Pressure nodal planes correspond to acoustic displacement anti-nodal planes and vice versa.

In one illustration, the microcarriers can be trapped in the multi-dimensional acoustic standing wave, e.g., remaining in a stationary position. The axial component of the acoustic radiation force drives the microcarriers, with a positive contrast factor, to the pressure nodal planes, whereas microcarriers with a negative contrast factor are driven to the pressure anti-nodal planes. The radial or lateral component of the acoustic radiation force is the force that traps the microcarriers, which can be larger than a combined effect of fluid drag force and gravitational force.

For small particles or emulsions, the fluid drag force $F_D$ can be expressed as:

$$\vec{F}_D = 4\pi\mu_f R_p(\vec{U}_f - \vec{U}_p)\left[\frac{1+\frac{3}{2}\hat{\mu}}{1+\hat{\mu}}\right] \quad (1)$$

where $U_f$ and $U_p$ are the fluid and particle velocity, $R_p$ is the particle radius, $\mu_f$ and $\mu_p$ are the dynamic viscosity of the fluid and particle, and $\hat{\mu}=\mu_p/\mu_f$ is the ratio of dynamic viscosities.

The buoyancy force $F_B$ can be expressed as:

$$F_B = \frac{4}{3}\pi R_p^3(\rho_f - \rho_p)g, \quad (2)$$

where g is the gravitational acceleration constant.

For a particle to be trapped in the acoustic standing wave, the force balance on the particle is zero, and therefore an expression for lateral acoustic radiation force $F_{LRF}$ can be found, which is given by:

$$F_{LRF}=F_D+F_B \quad (3)$$

For a particle of known size and material properties and for a given flow rate, this equation can be used to estimate the magnitude of the lateral acoustic radiation force.

The primary acoustic radiation force $F_A$ is defined as a function of a field potential U, where the field potential U is defined as, $F_A=-\nabla(U)$, where the field potential U is defined as:

$$U = V_0\left[\frac{\langle p^2\rangle}{2\rho_f c_f^2}f_1 - \frac{3\rho_f\langle u^2\rangle}{4}f_2\right] \quad (4)$$

and $f_1$ and $f_2$ are the monopole and dipole contributions defined by $$f_1 = 1 - \frac{1}{\Lambda\sigma^2},\ f_2 = \frac{2(\Lambda-1)}{2\Lambda+1}, \quad (5)$$

where p is the acoustic pressure, u is the fluid particle velocity, $\Lambda$ is the ratio of particle density $\rho_p$ to fluid density $\rho_f$, $\sigma$ is the ratio of particle sound speed $c_p$ to fluid sound speed $c_f$, and $V_0$ is the volume of the particle.

For a one dimensional standing wave, the acoustic pressure is expressed as:

$$p=A\cos(kx)\cos(\omega t), \quad (6)$$

where A is the acoustic pressure amplitude, k is the wavenumber, and $\omega$ is the angular frequency. In this case, there is only the axial component of the acoustic radiation force $F_{ARF}$, which is found to be $$F_{ARF} = V_0 k X\frac{A^2}{4\rho_f c_f^2}\sin(2kx), \quad (7)$$

where X is the contrast factor given by $$X = \left(\frac{5\Lambda-2}{1+2\Lambda} - \frac{1}{\sigma^2\Lambda}\right) \quad (8)$$

Particles with a positive contrast factor will be driven to the pressure nodal planes, and particles with a negative contrast factor will be driven to the pressure anti-nodal planes.

Figure 3B:
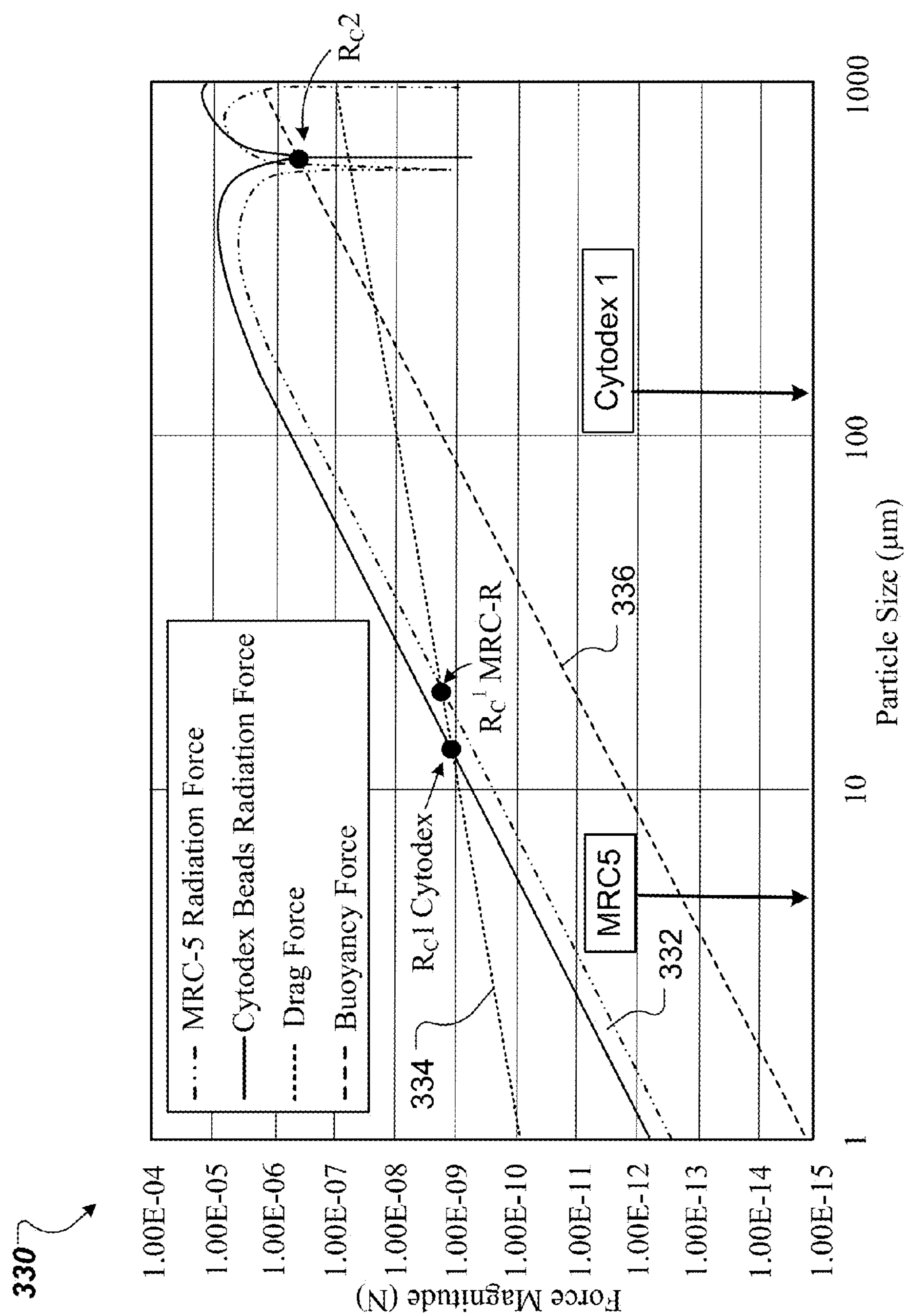
FIG. 3B shows a graph illustrating examples of drag force, buoyancy force and acoustic radiation force.

Numerical models can be developed for the calculation of the acoustic radiation force of the multi-dimensional acoustic standing wave for a particle without any restriction as to particle size relative to wavelength, such as Ilinskii and Zabolotskaya, Y. A. Ilinskii, E. A. Zabolotskaya, M. F. Hamilton, "Acoustic radiation force on a sphere without restriction to axisymmetric fields", Proceedings of Meetings on Acoustics, Vol. 19, 045004 (2013). These models can include the effect of fluid and particle viscosity to give an accurate calculation of the acoustic radiation force. FIG. 3B shows a graph 330 illustrating examples of acoustic radiation force 332, drag force 334, and buoyancy force 336 that scale with particle or cluster sizes.

The buoyancy force 336 is a particle volume dependent force, and is therefore negligible for particle sizes on the order of micron, but grows, and becomes significant for particle sizes on the order of hundreds of microns. The fluid drag force 334 scales linearly with fluid velocity, and therefore typically exceeds the buoyancy force 332 for micron sized particles, but is negligible for larger sized particles on the order of hundreds of microns. The acoustic radiation force scaling is different. When the particle size is small, the acoustic trapping force 332 scales with the volume of the particle. Eventually, when the particle size grows, the acoustic radiation force 332 no longer increases with the cube of the particle radius, and will rapidly vanish at a certain critical particle size. For further increases of particle size, the radiation force increases again in magnitude but with opposite phase. This pattern repeats for increasing particle sizes.

In some instances, when free floating cells and suspended microcarriers are flowing through the acoustophoretic separator, the acoustic radiation force for the cells, indicated by the MRC-5 Radiation Force curve, is smaller than the drag force, indicating that the cells are not trapped by the standing wave, and therefore will flow through the standing wave. On the other hand, the acoustic radiation force for the Cytodex beads is larger than the combined effect of gravity and fluid drag force on the beads, and therefore the beads will be trapped in the standing wave. Once the beads are trapped, they will cluster or agglomerate so that the effective bead cluster size grows until the gravity force becomes dominant resulting in gravitational settling and separation of the clustered beads.

In more detail, when a suspension is flowing through the system with primarily small micron sized particles, the acoustic radiation force may balance the combined effect of fluid drag force and the buoyancy force for a particle to be trapped in the standing wave. This can happen based on the contrast factor of a particle. In FIG. 3B, particles greater in size than 10 micron, labeled as Rc1, become trapped. Rc1 Cytodex is trapped earlier than Rc1 MRC-5 due to the acoustic radiation force acting on the particles. The graph then indicates that all larger particles will be trapped as well. Therefore, when small particles are trapped in the standing wave, particles will coalescence/clump/aggregate, resulting in continuous growth of effective particle size. As the particle size grows, the acoustic radiation force reflects off the particle, such that large particles will cause the acoustic radiation force to decrease. Particle size growth continues until the buoyancy or gravitational force becomes dominant, which is indicated by a second critical particle size, Rc2 at which size the particles will rise or sink, depending on their relative density with respect to the host fluid. As the particles rise or sink, they no longer reflect the acoustic radiation force, so that the acoustic radiation force then increases. Not all particles will drop out, and those remaining particles will continue to grow in size as well. This phenomenon explains the quick drops and rises in the acoustic radiation force beyond size Rc2. Thus, FIG. 3B explains how particles can be trapped continuously in a standing wave, grow into larger particles or clusters or clumps, and then eventually will rise or settle out because of increased gravity/buoyancy force.

For example, when a mixture of microcarriers and cultured cells in a fluid flows through the flow chamber, the microcarriers, e.g., with a diameter in the range of 20 to 250 μm, are trapped by the multi-dimensional acoustic standing wave to grown into clusters. As noted above, the multi-dimensional acoustic standing wave can result in a pressure field with hot spots at multiple maxima or minima of acoustic radiation potential and along multiple trapping lines perpendicular to a flow direction of the mixture flowing through the flow chamber. The microcarriers can be trapped along the trapping lines and agglomerate, aggregate, clump, or coalesce into multiple clusters at the hot spots that each include closely spaced microcarriers. The clusters can be adjacent to each other along the trapping lines. These clusters can form due to low flow, e.g., the particle/cluster Reynolds numbers can be approximately 1 or less. In some instances, particle/cluster Reynolds number represents the ratio of inertial forces to viscous forces and can be used to predict the flow velocity at which turbulence can occur. With these low flow rates, inertial forces of the trapped microcarriers become negligible and viscous forces are dominant throughout the flow. Thus, the forces which act on the clusters are different than Stokes' drag on a single microcarrier. Closely spaced microcarriers can have high shear forces for the clusters that prevent any significant flow between the microcarriers. The flow resistance around the clusters can be much lower than the shear resistance through the cluster, and the fluid trapped between the particles in the cluster is approximately stationary. In other words, the fluid flows around a microcarrier cluster rather than through it. The clusters can be also larger than the wavelength of the multi-dimensional acoustic standing wave along the trapping lines.

Figure 3C:
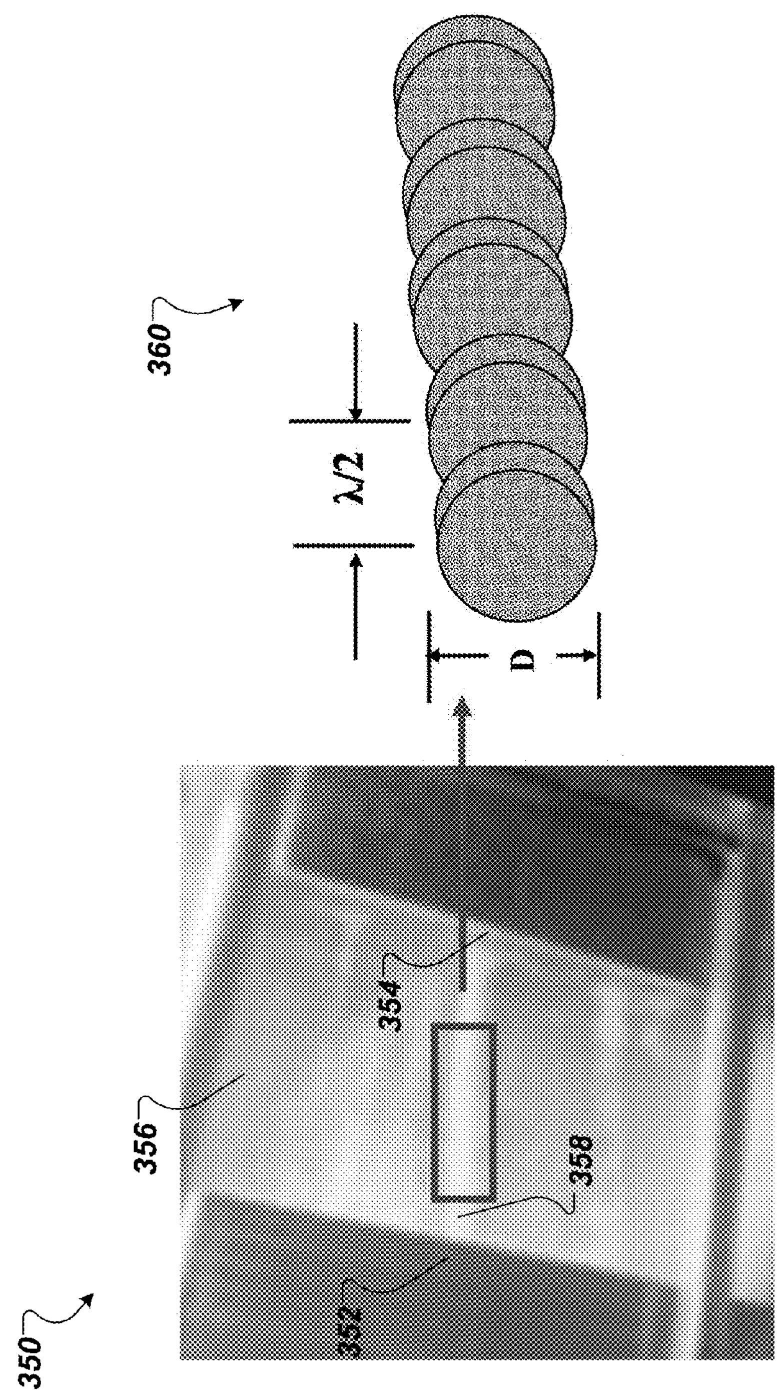
FIG. 3C is an example showing microcarrier packed clusters along trapping lines of a multi-dimensional acoustic standing wave.

FIG. 3C is an example of a process 350 showing microcarrier-packed clusters located along a trapping line of a multi-dimensional acoustic standing wave. The multi-dimensional acoustic standing wave is generated by an acoustic transducer 352 and a reflector 354 positioned on opposite walls of a flow chamber 356. When the mixture of microcarriers and cultured cells flow through the flow chamber 356, the microcarriers are trapped and then agglomerate, aggregate, clump, or coalesce into clusters along the trapping lines 358. The clusters can in a "hockey-puck" formation, as illustrated by a diagram 360. Along the trapping lines, more microcarriers or clusters or mass can be fit in a same projected area. A diameter D of the formed clusters can be around multiple wavelengths of the multi-dimensional acoustic standing wave, i.e., 1-5, or bigger depending on the mode of perturbation.

As the clusters of microcarriers grow, they begin to overcome the trapping force of the multi-dimensional acoustic standing wave and fall out of the standing wave due to gravity separation or rise out due to buoyancy separation. This can set up a continuous separation process and allows the separation of the microcarriers from the fluid stream to occur continuously.

Figure 3D:
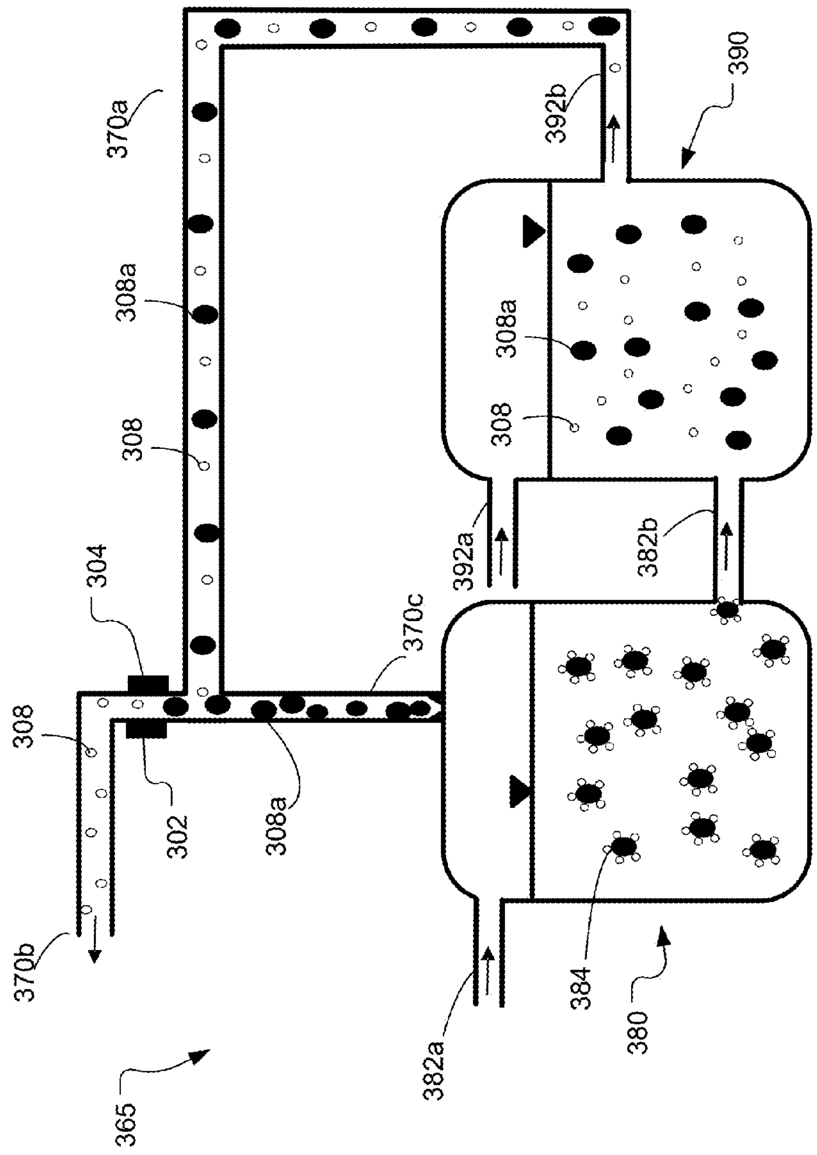
FIG. 3D is an example of a system for separating cells from cellular supporting material such as microcarriers.

FIG. 3D shows another example apparatus 365 with an acoustic separator 370, a bioreactor chamber 380 containing fluid that includes cells cultured on cellular supporting material, and a processing chamber 390 in which the cells are being cleaved from the cellular supporting material. In this example, fluid that includes nutrients, inoculant, and/or cellular supporting material flows into the bioreactor chamber 380 via inlet 382*a* such that microcarriers settling out in the apparatus while cells can pass through. The bioreactor chamber is maintained at conditions conducive to encouraging the growth of desired cells on the cellular supporting material 384. An outlet 382 may serve as a conduit for such fluid containing cells cultured on cellular supporting material 384 to flow into the processing chamber 390. Here, backflush of such fluid may be reduced or minimized. The processing chamber 390 generally prepares the fluid for acoustic separation by separating the cells from the cellular supporting material 384, e.g., by the use of proteolytic enzymes such as trypsin or collagenase which can be introduced through an intake 392*a*. Processing chamber 390 may incorporate a stirring process (e.g., by means of a magnetic stirrer) to facilitate the cleaving of cells from the cellular supporting material 384.

The cleaving process may generally include a biochemical process that may require a specific residence time. In some systems, fluid can be recirculated to intake 392*a* to achieve a desired residence time for fluid in the system. In general, processed fluid may exit from outlet 392*b* into a channel 370*a*. As illustrated, in this channel 370*a*, cells 308 and cellular supporting material 308*a* are no longer attached to each other but are mixed in the same liquid. Thereafter, transducer 302 and reflector 304 placed on opposite walls of the separation chamber 370 may be operated to create an example multi-dimensional acoustic standing wave, as discussed above, trapping the cellular supporting material 308*a*. In one example, apparatus 365 may include a dedicated acoustic chamber with transducer 302 and reflector 304 placed on opposite walls. In this dedicated acoustic chamber, acoustic separation by the multidimensional standing waves created therein is implemented. Cells flow through the multi-dimensional acoustic standing wave and exit via an outlet 370*b*. The cellular supporting material 308*a* is trapped in the multi-dimensional acoustic standing wave until agglomeration causes them to reach a size at which gravity overcomes the acoustic forces and the agglomerated cellular supporting material 308*a* sinks—flowing through outlet 370*c* back into the bioreactor. As a result, cells 308 may be separated from the cellular supporting material 308*a*.

As an example of separation of microcarriers from cultured cells using a multi-dimensional acoustic standing wave, a filtering process is carried out by experiments in which MRC-5 cells cleaved from Cytodex 1 microcarrier beads. A mixture fluid includes the MRC-5 cells with a concentration of about 1.6*10^6 cells/mL and Cytodex 1 microcarrier beads with a concentration of about 5 g/L.

An acoustophoretic device, e.g., the apparatus 300 of FIG. 3A, was used. An acoustic transducer was driven at a constant voltage level, e.g., 50 V. The transducer operating frequency and flow rate through the device were varied in different tests. Table 1 shows a list of tests in which the operating frequency and total experiment test time and processed volume of cells and beads are defined.

TABLE 1

Testing conditions for acoustic separation

| Testing Matrix | | Feed flow rate (mL/min) 30 | 60 | 120 |
|---|---|---|---|---|
| Operating Frequency (MHz) | 2 | Test 1: 30 min, 900 ml | Test 2: 30 min, 1800 ml | Test 3: 19 min, 2300 ml |
| | 1 | Test 4: 30 min, 900 ml | Test 5: 30 min, 1800 ml | |

Test 6 was performed with a second pass of the flowed fluid (for further enrichment), captured from the cell outlet stream, run after Test 4 was run once at a condition with 1 MHz operating frequency and 30 mL/in flow rate.

Figure 4:
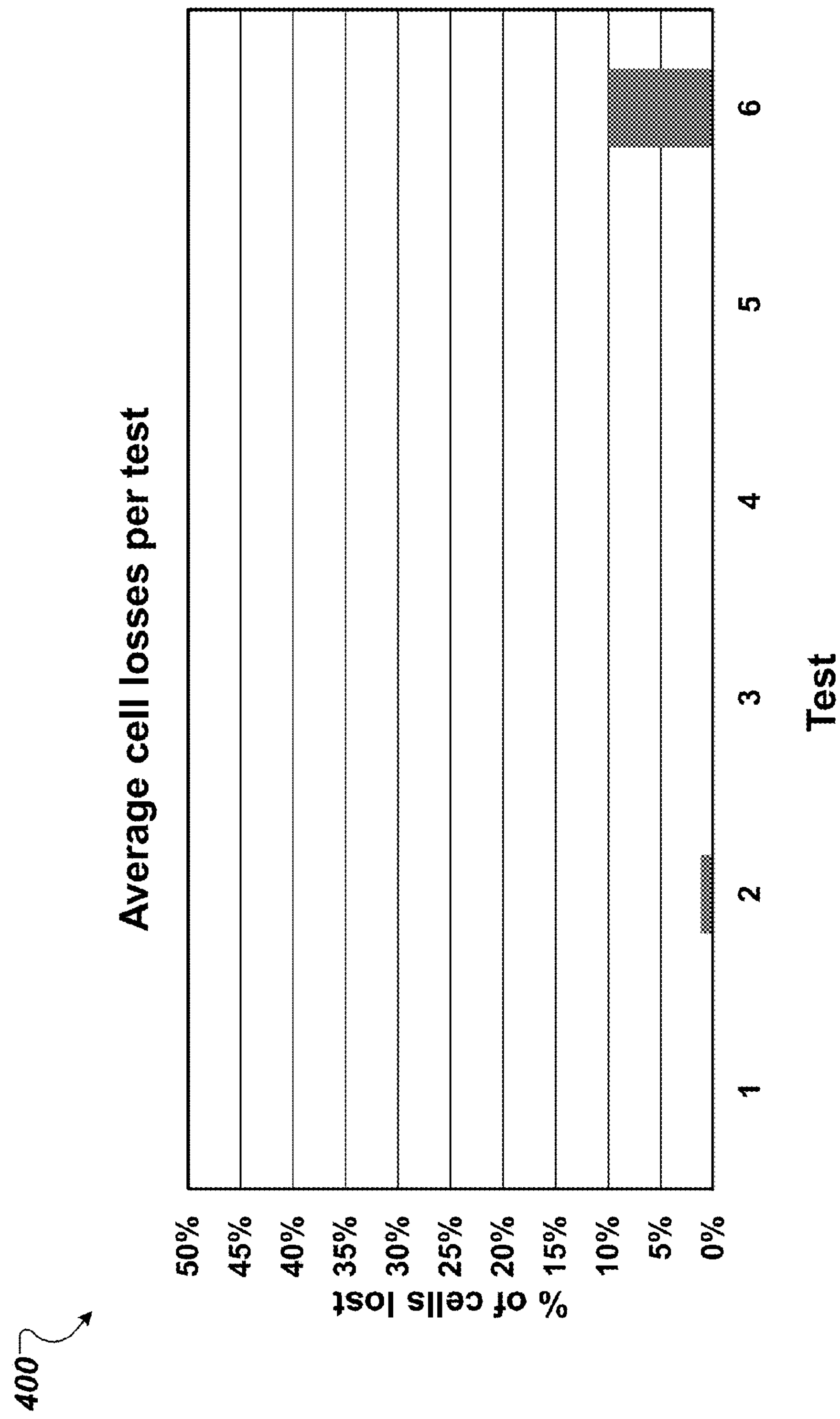
FIG. 4 shows an experimental result of average cell losses in acoustic separation tests.

The performance of the acoustic separation was tested by measuring cell concentration (e.g., by nucleus counter) and microcarrier bead concentration (e.g., by microscope). FIG. 4 shows results of average cell losses per test. As demonstrated, the passage rate of cells through the acoustic wave separation (AWS) system is generally greater than 90%. In particular, the results from Test 1 show that: 1) about 100% passage of cells through the device is measured; 2) clumping and dropping of microcarriers by acoustics are observed; 3) significant removal of microcarriers is observed with microscope. The results of Test 2 show that: 1) clumping and dropping of microcarriers by acoustics are observed; 2) little change in microcarriers is observed with microscope. Compared to the result of Test 1, higher flow rate in Test 2 causes less trapping force and less microcarrier removal. Test 3 yields similar results to those from Test 2. Results from Test 4 demonstrate that the microcarrier drop rate can be higher than Test 1 when the operating frequency is lowered to 1 MHz. Similarly, significant removal of microcarriers is observed from a microscope. When the flow rate increases to 60 mL/min, little change in removal of microcarriers is observed in Test 5. In Test 6, about 90% passage of cells through the device is measured. Additionally, clumping and dropping of microcarriers by acoustics are observed. Moreover, no microcarriers are observed with microscope in the outlet stream, which indicates that the first run in Test 4 removes most of the microcarriers and a small amount of the remaining microcarriers are completely trapped and separated by the device in the second run.

The test results show 90% or greater passage of cells through the acoustophoretic device measured at all conditions, the ability to capture microcarriers observed at all test conditions, and about 100% removal of microcarriers after two stages of acoustic separation.

Figure 5:
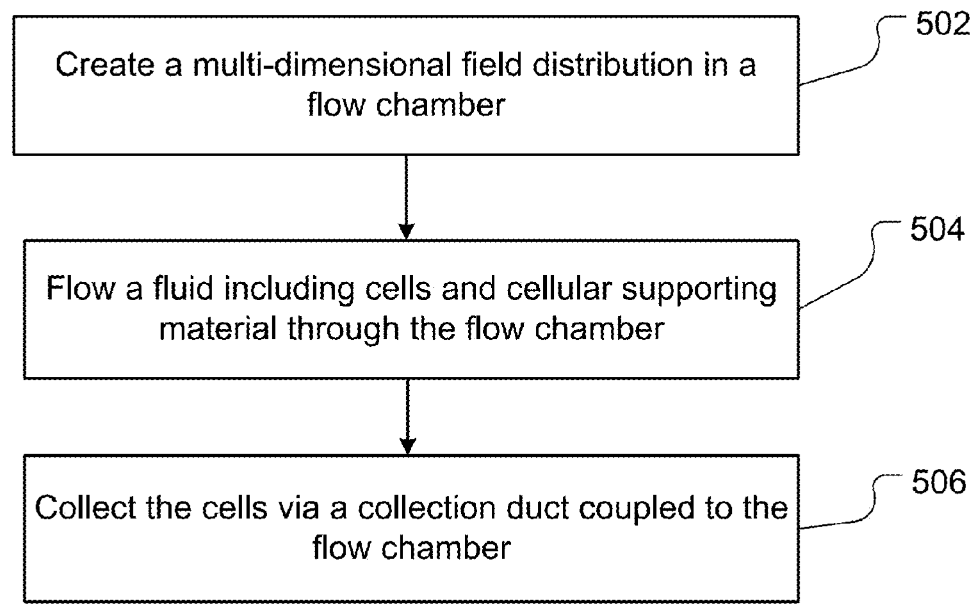
FIG. 5 is a flowchart showing an example of a cell separation process.

FIG. 5 is a flowchart showing an example of a cell separation process 500. The cell separation process 500 can be performed by an acoustophoretic device, e.g., the apparatus 300 of FIG. 3A, that provides a multi-dimensional acoustic standing wave. The process can separate a particulate, e.g., cellular supporting materials such as microcarriers, from a fluid including cells adherent and cultured on the particulate but cleaved therefrom prior to entry into the acoustophoretic device.

A multi-dimensional acoustic standing wave is provided in a flow chamber of the acoustophoretic device (502). The acoustophoretic device includes at least one acoustic transducer positioned on a wall of the flow chamber and configured to generate an acoustic wave when driven by a power signal, e.g., a voltage signal at a driving frequency, e.g., sine wave, square wave, pulsed wave. The acoustophoretic device also includes a respective reflector positioned on the wall opposite to the acoustic transducer and configured to reflect the acoustic wave to create a multi-dimensional acoustic standing wave within the flow chamber and between the acoustic transducer and the reflector.

As noted above, the acoustic transducer includes a vibrating material such as a piezoelectric material, e.g. PZT8. The acoustic transducer can be configured such that the vibrating material vibrates at a higher order vibration mode when driven by the power signal. The higher order vibration mode can be greater than (2, 2), thus a multi-dimensional acoustic standing wave, e.g., 3-dimensional, can be generated.

A fluid including the cells and the cellular supporting material is flowed through the flow chamber (504). The mixture can be flowed through the flow chamber at a rate of at least 0.25 liters per hour. The mixture includes suspending particulate and free-floating cells. The multi-dimensional acoustic standing wave can be tuned to trap the particulate and allow the cells to flow through the fluid stream. In some instances, flow rate can be increased significantly through scaling of the flow chamber (504), e.g., 50 L/hr units have been built and tested successfully.

As discussed above, the multi-dimensional acoustic standing wave can result in a pressure field with hot spots at multiple maxima or minima of acoustic radiation potential and along multiple trapping lines perpendicular to a flow direction of the mixture. The acoustic radiation force can have an axial force component and a lateral force component that are of the same order of magnitude. The particulate can be trapped by the acoustic radiation force and then agglomerate, aggregate, clump, or coalesce into multiple clusters at the hot spots that each include closely spaced particles. The clusters can be adjacent to each other along the trapping lines.

The multi-dimensional acoustic standing wave results in pressure nodal planes including the hot spots at the minima of the acoustic radiation potential for particles with positive acoustic contrast, and pressure anti-nodal planes including the hot spots for particles with negative acoustic contrast. Trapping may generally occur at minima of the acoustic radiation potential, for particles with positive acoustic contrast these correspond to pressure nodal planes (e.g., cells) for particles with negative contrast these correspond to anti-nodal planes (e.g. lipids). In some cases, the particulate includes a reflective core and is driven in the pressure field to the pressure nodal planes when the mixture flows through the flow chamber. In some cases, the particulate includes an absorbent core and is driven in the pressure field to the pressure anti-nodal planes when the mixture flows through the flow chamber. The particulate can be continuously trapped by the multi-dimensional acoustic standing wave to agglomerate, aggregate, clump, or coalesce together, and subsequently rise or settle out of the fluid due to buoyancy or gravity forces, and eventually exit the flow chamber.

In this example, the cells are then collected to a collection duct coupled to the flow chamber (506). As the particulate is continuously trapped in the flow chamber by the multi-dimensional standing wave and the cells freely flow through the flow chamber with the fluid, the separated fluid will include the cells with little particulate or none.

In some examples, the particulate has a higher density than the fluid medium. For example, the particulate includes microcarriers with a density of about 1.02 to 1.1 g/cm^3. The particulate can be trapped to agglomerate, aggregate, clump, or coalesce together, and subsequently sink down due to gravity forces. In some cases, the mixture flows upward so that the cells are collected to the collection duct coupled to the top end of the flow chamber and the dropped particulate clusters or clumps are collected to a separate collection duct coupled to a bottom end of the flow chamber. In some cases, the mixture flows downward. To separate the cells and the dropped particulate clusters, one or more filters can be installed on the bottom end of the flow chamber to stop the dropped particulate clusters, and the cells are collected into a subsequent chamber under the filters.

In some examples, the particulate has a lower density than the fluid medium. For example, the particulate includes bubbles or microbubbles. The particulate is trapped to agglomerate, aggregate, clump, or coalesce together, and subsequently rise due to buoyancy forces. In this cases, the mixture is flowed downward so that the cells are collected to the collection duct coupled to the bottom end of the flow chamber. Meanwhile, the trapped microcarriers may also be collected, for example, for reuse and/or recirculation.

In some implementations, the separated fluid after step 506 is flowed in one or more passes through the flow chamber. As the multi-dimensional acoustic standing wave keeps trapping the particulate, the second separated fluid can include none of the particulate.

Instead of microcarriers, some implementations may use microbubbles as cellular supporting materials. The microbubbles can be composed by a shell of biocompatible materials and ligands capable of linking to the cells to grow, including proteins, lipids, or biopolymers, and by a filling gas. Generally, low density fluids may be used—for relative ease of manufacturing. The microbubble shell may be stiff (e.g., denaturated albumin) or flexible (phospholipids) and presents a thickness from 10 to 200 nm. The filling gas can be a high molecular weight and low-solubility filling gas or liquid (perfluorocarbon or sulfur hexafluoride), which can produce an elevated vapor concentration inside the microbubble relative to the surrounding fluid, such as blood, and increase the microbubble stability in the peripheral circulation. The microbubble shell can have a surface coating such as a lipid layer. The lipid layer may be utilized as scaffolds or substrates for material growth such as cells or biomolecules. Active groups may be easier to conjugate directly to the glass surface. The microbubbles may have a diameter in a range of 2 to 6 micrometers. Enzyme cleaving may use proteolytic enzymes such as trypsin or collagenase to cleave the adherent cells from the microbubbles. The coated microbubbles may have a negative contrast factor and, through the use of acoustophoresis, can migrate to the antinodes of the multi-dimensional acoustic standing wave and thus be trapped and separated from the adherent materials.

A number of embodiments of the invention have been described. Nevertheless, it will be understood that various modifications may be made without departing from the spirit and scope of the invention. Accordingly, other embodiments are within the scope of the following claims.

The invention claimed is:

1. A method of separating micro-sized cellular supporting material from cells cultured on the micro-sized cellular supporting material, the method comprising:

flowing a fluid containing the micro-sized cellular supporting material and the cells through a flow chamber;

driving at least one acoustic transducer to launch an acoustic wave from the acoustic transducer positioned at one side of the flow chamber to a reflector positioned across the flowing fluid from the acoustic transducer to create, in the flow chamber, a multi-dimensional acoustic standing wave that includes first spatial locales where acoustic pressure amplitude is elevated compared to when the acoustic transducer is turned off, and second spatial locales where acoustic pressure amplitude is substantially identical to when the acoustic transducer is turned off;

preferentially trapping, the micro-sized cellular supporting material or the cells at the first or second spatial locales inside the flow chamber; and collecting cells separated from the micro-sized cellular supporting material via a first collection duct coupled to the flow chamber.

2. The method of claim 1, wherein collecting cells is performed without turning off the acoustic transducer.

3. The method of claim 1, wherein preferentially trapping the micro-sized cellular supporting material comprises trapping in at least one of the first spatial locales or in at least one of the second spatial locales to reduce a level of the micro-sized cellular supporting material in the fluid.

4. The method of claim 1, further comprising distinguishing between viable cells and non-viable cells based on at least one of compressibility, size, or density.

5. The method of claim 4, further comprising reducing an amount of the non-viable cells in fluid by preferentially trapping the non-viable cells.

6. The method of claim 5, wherein preferentially trapping the non-viable cells comprises preferentially trapping the non-viable cells at either the first spatial locales or the second spatial locales.

7. The method of claim 4, further comprising: reducing an amount of the viable cells in the fluid by preferentially trapping the viable cells.

8. The method of claim 4, further comprising: increasing a contrast factor between the viable and non-viable cells by changing acoustic properties of the viable cells or the non-viable cells or the fluid.

9. The method of claim 8, wherein changing the acoustic properties of either the viable or the non-viable cells comprises changing cell volumes of viable cells by changing salt concentrations in the fluid.

10. The method of claim 1, further comprising introducing an additive which enhances aggregation of the cellular supporting material into the flow chamber.

11. The method of claim 1, further comprising recirculating the micro-sized cellular supporting material to a culturing chamber coupled to the flow chamber.

12. The method of claim 1, further comprising: processing the collected cells for infusion into a subject patient.

13. The method of claim 1, subsequent to preferentially trapping, allowing the trapped cells or micro-sized cell-supporting material to rise or settle out of the fluid due to a buoyance or gravity force such that the trapped cells or micro-sized cell-supporting material then exit the flow chamber.

14. The method of claim 1, wherein the micro-sized cellular supporting material comprises a particulate having a core that is more acoustically reflective than a shell of the particulate, and wherein preferentially trapping the micro-sized cellular supporting material comprises preferentially trapping the particulate at one of the first spatial locales inside the flow chamber.

15. The method of claim 1, wherein the micro-sized cellular supporting material includes a particulate having a core that is less acoustically reflective than a shell of the particulate, and wherein the preferentially trapping the micro-sized cellular supporting material comprises preferentially trapping the particulate at one of the second spatial locales inside the flow chamber.

16. The method of claim 1, further comprising:

flowing the fluid through the flow chamber vertically upwards, and collecting the cells via the first collection duct, wherein the micro-sized cellular supporting material clump, cluster, or agglomerate such that the micro-sized cellular supporting material sinks down to a second collection duct coupled to the flow chamber, the second collection duct being different from the first collection duct.

17. The method of claim 1, further comprising:

flowing the fluid through the flow chamber vertically downwards, and collecting the cells via the first collection duct wherein the micro-sized cellular supporting material settles to a second collection duct coupled to the flow chamber, the second collection duct being different from the first collection duct.

18. The method of claim 1, wherein the micro-sized cellular supporting material comprises microcarriers, and wherein at least one of the microcarriers comprises a sphere with a diameter of about 30 to 300 μm and comprises at least one of DEAE (N, N-diethylaminoethyl)-dextran, glass, polystyrene plastic, acrylamide, collagen, or alginate.

19. The method of claim 1, wherein the micro-sized cellular supporting material comprises microbubbles that have a surface coating for growth of the cells.

20. The method of claim 1, wherein the cells comprise T-cells, MRC-5 cells or stem cells.

21. The method of claim 1, wherein the micro-sized cellular supporting material comprises particulates.

22. The method of claim 21, wherein the particulates comprise spheres with a diameter of 20 to 200 μm.

23. The method of claim 21, wherein the particulates comprise spheres with a diameter of 90 to 300 μm.

24. The method of claim 21, wherein the particulates comprise microbubbles with a diameter between 2 to 6 μm.

* * * * *